United States Patent [19]

Wieland

[11] 4,150,560
[45] Apr. 24, 1979

[54] MEASURING CELL FOR THE CONTINUOUS DETERMINATION OF A LIQUID, ESPECIALLY A BEVERAGE FLOWING THROUGH A PIPE

[76] Inventor: Dieter Wieland, Oststrasse 1, 4000 Düsseldorf, Fed. Rep. of Germany

[21] Appl. No.: 820,999

[22] Filed: Aug. 1, 1977

[30] Foreign Application Priority Data

Aug. 4, 1976 [DE] Fed. Rep. of Germany ....... 2634971

[51] Int. Cl.² .............................................. G01N 7/14
[52] U.S. Cl. ...................................................... 73/19
[58] Field of Search .................................. 73/19, 61 R

[56] References Cited
U.S. PATENT DOCUMENTS

| | | | |
|---|---|---|---|
| 3,060,722 | 10/1962 | Migdal et al. ............................ | 73/19 |
| 3,077,765 | 2/1963 | Dijkema .................................... | 73/19 |
| 3,177,706 | 4/1965 | Shuman et al. ....................... | 73/61 R |
| 3,673,853 | 7/1972 | Griswold et al. ......................... | 73/19 |

Primary Examiner—Stephen A. Kreitman
Attorney, Agent, or Firm—Sprung, Felfe, Horn, Lynch & Kramer

[57] ABSTRACT

A measuring cell for the continuous determination of the carbon dioxide content of a flowing liquid. The cell comprises an inner chamber having a first substantially cylindrical portion, an input conduit for the feeding of liquid to the cell and a discharge line for the removal of the liquid. The input conduit has a portion entering at one end of the first portion tangentially to its peripheral surface and a discharge line has a portion disposed in a direction of the longitudinal axis of the first portion and entering the chamber below the input conduit. The input conduit is constricted at or immediately ahead of the point of entry and a device is disposed within the chamber in the immediate vicinity of the point of entry or directly ahead of the entry of the discharge line for measuring the temperature of the liquid and a second device is disposed at the inner wall of the first portion for measuring the outgassing pressure of the liquid. The two devices produce electrical signals corresponding to the measured values and conductors carry the signals out of the chamber of the measuring cell.

8 Claims, 4 Drawing Figures

MEASURING CELL FOR THE CONTINUOUS DETERMINATION OF A LIQUID, ESPECIALLY A BEVERAGE FLOWING THROUGH A PIPE

BACKGROUND OF THE INVENTION

The subject of the invention is a measuring cell for the continuous determination of the carbon dioxide content of a liquid flowing through a pipe, especially a beverage.

It is known to determine the content of carbon dioxide in beer and other carbonated beverages by analyzing individual samples by chemical or static physical methods. These methods, however, are difficult and they permit no more than a "spot check" of the liquid in question.

It is furthermore known to determine the carbon dioxide content of a liquid continuously by means of a diffusion cell inserted into a pipe line wherein an inert carrier gas is fed into and out of the cell and the carbon dioxide content of the output gas is measured by determining the infrared absorption. This known method, however, is very expensive and contains many sources of error.

It has also become known to continuously determine the carbon dioxide content of a liquid flowing through a pipe by means of an apparatus in which a partial stream of the liquid is carried by a measuring pipe through a measuring cell in which an outgassing of the liquid takes place, a device for measuring the static liquid pressure being provided ahead of the measuring cell, and a device for measuring the temperature and one for measuring the outgassing pressure being provided within the measuring cell, the measurements being transmitted continuously to an evaluating means.

In this known system, the second chamber of a differential pressure meter serves as the measuring cell, while the static liquid pressure is measured in the first chamber of the differential pressure meter. The measurement of the pressure is performed mechanically, and all of the measurements are evaluated and indicated in a mechanical system. The accuracy and speed of measurement achievable by this known system, however, are very limited.

SUMMARY OF THE INVENTION

The object of the present invention is to provide an improved measuring cell for the continuous determination of the carbon dioxide content of a liquid flowing through a pipe.

This and other objects are accomplished by the invention by giving the interior of the said measuring cells substantially the shape of a cylinder, and having an entrance conduit leading into one end of this cylinder tangentially to its periphery, while providing at the other end of the said cylinder a discharge conduit for discharging said liquid in the direction of the axis of the cylinder, the said entrance conduit having a constriction at or immediately ahead of the point of entry, and by providing within the said cylinder, in the immediate vicinity of the point of entry or directly ahead of the orifice of the said discharge conduit a device for measuring the temperature of the said liquid, while also providing in or on an inside wall of said cylinder a device for measuring the outgassing pressure of the liquid, the devices for measuring the temperature and the outgassing pressure emitting electrical signals which are carried by conductors to the outer chamber of the said measuring cell.

The special construction of the measuring cell of the invention brings about a constant, very uniform, unbroken emission of carbon dioxide from the liquid which is revolving in a thin layer, and thus a very precise and reproducible measurement is possible.

The temperature is measured within the measuring cell at a point at which liquid is always present during operation. Since the equalization of the temperature throughout the measuring cell always takes place very rapidly, either the area following the input orifice or the area ahead of the discharge orifice is well suited for this purpose. Since the temperature measurement has a strong influence on the result, it may be desirable to provide the measuring cell with a thermal insulating jacket.

In an especially advantageous embodiment of the invention, a particularly desirable guidance of the liquid in the measuring cell is brought about by providing the measuring cell with a funnel-like taper towards the discharge, at least adjacent the discharge orifice.

The device for measuring the outgassing pressure can best be disposed on or in the peripheral surface of the cylinder. In this manner an especially good transmission of the gas pressure from the interior of the measuring cell to the measuring apparatus is achieved.

The measuring cell of the invention opens up a great number of possible applications, particularly in the beverage manufacturing field. Examples are:

1. Carbon dioxide measurement in beer flowing through pipes at the end of filtration or between the first and second filters.
2. Detection of the beer phase and water phase in the first runnings and last runnings through indications of the carbon dioxide content.
3. Controlled blending of beer from storage tanks with different carbonic acid contents in the beer. Controlled carbonation of beer, manual or automatic.
5. Simplified production control.
6. Saving of carbonic acid gas in the production of carbonated, non-alcoholic beverages through a feed-back controlled corrective input of carbon dioxide.

It is also possible by means of the measuring cell of the invention to measure the carbon dioxide content of a liquid at a normal atmospheric pressure on the liquid. This means that the measuring cell can also be used for a very rapid measurement of individual samples. For this purpose, for example, the content of a glass or of a bottle can be aspirated via a measuring tube through the measuring cell and evaluated.

BRIEF DESCRIPTION OF THE DRAWINGS

An example of the embodiment of the measuring cell of the invention is further explained herewith in reference to the appended drawings wherein.

DETAILED DESCRIPTION OF THE INVENTION

Figure 1:
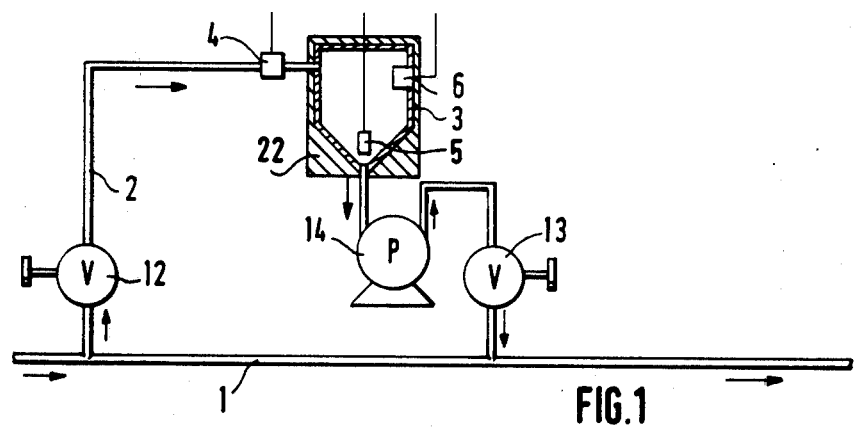
FIG. 1 is a circuit diagram of an apparatus for the continuous determination of the carbon dioxide content of a liquid by means of a measuring cell in accordance with the invention.

In the apparatus represented in FIG. 1, the carbonated liquid to be tested—for example, beer, mineral water or the like—is flowing through a main pipe 1. A partial stream is tapped off from the main stream of the liquid through a measuring line 2 which leads through a measuring cell 3 and back to the main line 1. At the beginning and end of the measuring line 2 there are the shut-off valves 12 and 13, and the liquid is pumped through the measuring cell 3 by a circulating pump 14. The static pressure $P_L$ of the flowing liquid is measured by a pressure measuring device 4 in measuring line 2 ahead of the entrance to the measuring cell 3. In addition, the outgassing pressure $P_E$ is measured with another pressure measuring device 6 and the temperature is measured with a temperature measuring device 5 within the measuring cell 3 which will be further explained below. The pressure measuring devices 4 and 6 operate on the piezo-resistive principle with an accuracy of better than 0.01%. The electrical signals put out by the pressure measuring devices and temperature measuring devices can be evaluated according to known techniques.

Figure 2:
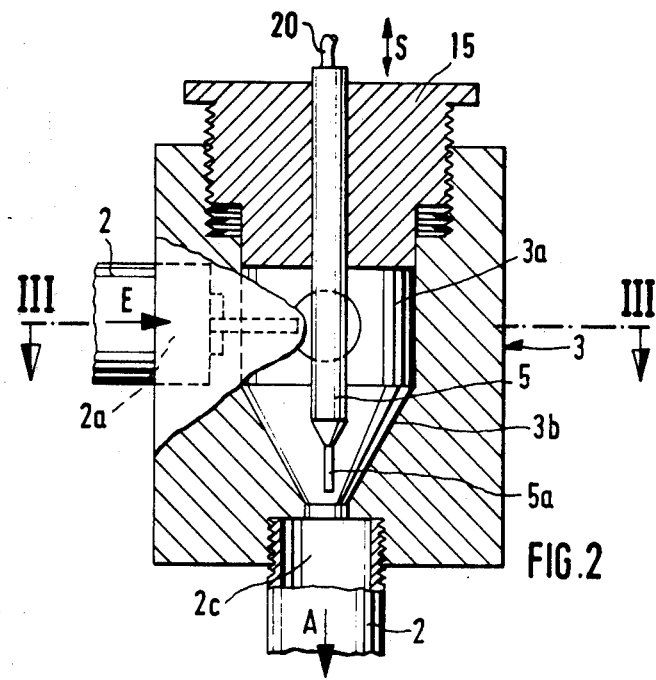
FIG. 2 is a diagrammatic representation of a measuring cell of the invention in a longitudinal, vertical cross section taken along line II—II of FIG. 3.
Figure 3:
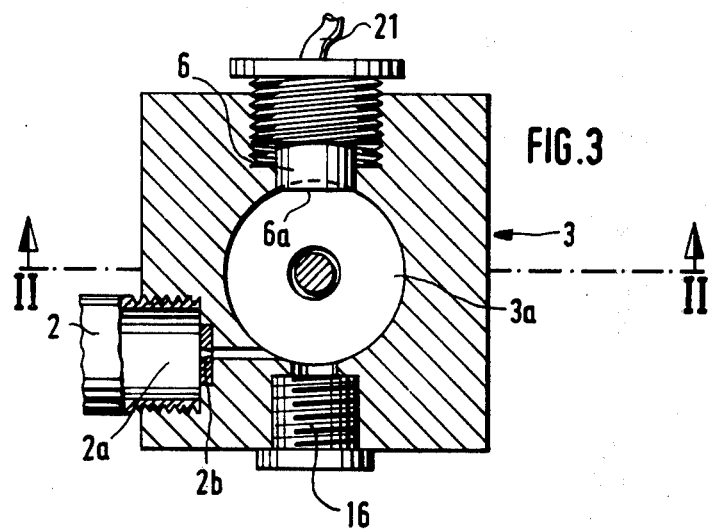
FIG. 3 is a cross sectional view taken through the measuring cell of FIG. 2 along line III—III.

The measuring cell is further represented in FIGS. 2 and 3.

The liquid being measured flows from the measuring line 2 to the entrance orifice 2a of the measuring cell 3 where it first passes through a diaphragm or nozzle 2b and then flows into the inner chamber 3a, which is of cylindrical shape in its upper portion, at a tangent to the inside wall of the inner chamber (see FIG. 3). The cylindrical upper portion of the inner chamber 3a is adjoined at the bottom by a funnel-shaped portion 3b at whose bottom end is the outlet 2c which in turn is adjoined by the measuring line 2 which leads back to the main line 1.

As a result of this configuration of the inner chamber of the measuring cell 3, the injected liquid undergoes a rotary movement, moving along the inside wall of the measuring cell and being driven downwardly, and finally leaving the measuring cell through the funnel-like portion 3b and the outlet 2c in the direction A. In the rotatory movement, a thin layer of liquid forms on the inner wall of the inner chamber 3a and the carbon dioxide gases out of the liquid into the inner chamber. The pressure measuring device 6 is screwed into the side of the measuring cell 3 and is so disposed that a pressure receiving membrane 6a lies in the peripheral surface of the cylindrical portion 3a of the inner chamber. Adjustment of the position of the membrane 6a can be accomplished by screwing the measuring device further inwardly or outwardly. The pressure that builds up in the inner chamber acts through the rotating liquid layer on the membrane 6a of the pressure measuring device 6 and it has been found that a very sensitive measurement of pressure is obtained in this manner.

The inner chamber of the measuring cell 3 is closed off at the top by a threaded cap 15. The volume of the inner chamber 3a can be varied according to the depth to which this cap is screwed. This is particularly advantageous whenever the apparatus is to be used in measuring the carbon dioxide content of different liquids or beverages having different carbon dioxide yielding characteristics. The measuring cell 3 can be adapted to these different characteristics by varying the volume of the inner chamber 3a.

A temperature measuring device 5 is disposed on the cap 15 and is so constructed that its temperature sensor 5a at its bottom end is located within the funnel-shaped portion 3b of the inner chamber, directly in front of the outlet 2c. This assures that the temperature sensor 5a will be located at a point at which liquid is always present during operation.

The electrical signals from the pressure measuring device 6 are carried by a conductor 21 and the electrical signals of the temperature measuring instrument are carried by a conductor 20 to the outer chamber of the measuring cell 3.

To protect the measuring cell 3 against fluctuations of the outside temperature, the cell can be provided, as indicated in FIG. 1, with a thermal insulating jacket 22.

An opening is furthermore provided in the sidewall of the measuring cell 3 leading into the inner chamber at the point of entry of the liquid, and it is stopped by a transparent plug 16. Thus a window is obtained, through which the processes taking place inside of the measuring cell 3 can be observed.

Of special importance is the orifice plate or nozzle 2b which is disposed in the entrance 2a of the measuring cell. It has proven to be advantageous for the aperture of the nozzle or orifice to be variable, since in this manner, as in the case of the variation of the volume of the measuring cell, an adaptation to various carbon dioxide yielding characteristics of different liquids can be achieved. The change of the aperture size can be accomplished simply by replacing the nozzle or orifice plate. It is also possible, however, to provide a nozzle or plate having an adjustable orifice by using, for example, a central spindle. An orifice plate diaphragm is best made such that it has on the side facing the incoming liquid a slightly greater diameter decreasing uniformly in the direction of flow. In this manner the clogging of the nozzle when used with liquids that may contain solid particles can be prevented.

Figure 4:
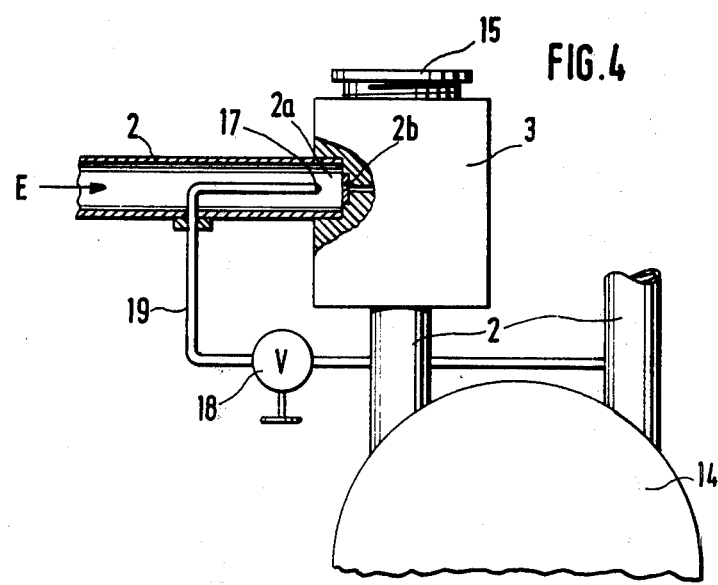
FIG. 4 shows a portion of the apparatus of FIG. 1 in an embodiment which includes a device for cleaning the nozzle of the measuring cell.

It has furthermore proven desirable, however, when the apparatus is to be used with liquids which may contain solid particles, such as beer or fruit juice beverages, for example, to provide a means for clearing the nozzle 2b of the measuring cell 3. Such a means is diagrammatically represented in FIG. 4. It has a nozzle 17 which is disposed just ahead of the nozzle 2b in the direction of flow, and it is connected to a conduit 19 which is connected through a valve 18 to the measuring line 2 between the pump 14 and the main line 1 which is not represented. When liquid is being pumped through the measuring line 2, the opening of the valve 18, which can also be constructed in the form of a solenoid valve, will produce a fine jet of the liquid from the nozzle 17, directed under high pressure against the nozzle or orifice 2b. This will result in a rapid clearing of the clogged constriction. Of course, this clearing process can be automated such that the valve 18 will be actuated automatically whenever maximum or minimum levels of the carbon dioxide content are reached, thereby producing a clearing action.

The evaluation of the measured parameters sets out from the known fact that the carbon dioxide content in liquid can be represented by the following general formula:

$$\text{Amount of } CO_2 = f\left(\frac{P_E}{P_L, T}\right)$$

In this formula, $P_E$ is the outgassing pressure of the liquid, $P_L$ is the beverage pressure in the line, and T is the temperature of the liquid. The apparatus constants contained in the above-named function f can be determined by comparative measurements.

It will be appreciated that the instant specification and claims are set forth by way of illustration and not limitation, and that various modifications and changes may be made without departing from the spirit and scope of the present invention.

What is claimed is:

1. A measuring cell for the continuous determination of the carbon dioxide content of a flowing liquid, especially a beverage, comprising inner chamber having a first substantially cylindrical portion, an input conduit for the feeding of liquid to the cell and having a portion entering at one end of the first portion tangentially to its peripheral surface, a discharge line for the removal of the liquid having a portion disposed in the direction of the longitudinal axis of the first portion and entering the chamber below said one end, wherein the input conduit having means for constricting same at or immediately upstream of the point of entry comprising an orifice, means for clearing the orifice of the constricting means comprising a spray nozzle disposed immediately upstream of the orifice and having the output thereof aligned with the orifice in the direction of flow, a conduit connected to the spray nozzle and receptive of liquid under high pressure and a valve in said conduit for selectively effecting the blowing of high-pressure liquid from said spray nozzle into the orifice to clear same, first means disposed within the said chamber in the immediate vicinity of the point of entry or directly upstream of the entry of the said discharge line for measuring of the temperature of the liquid, second means disposed at the inner wall of the first portion for measuring the outgassing pressure of the liquid, wherein said first and second means produce electrical signals corresponding to the measured values and conductors for carrying the signals out of the chamber of the measuring cell.

2. The measuring cell of claim 1, wherein said inner chamber further comprises a second downwardly tapering conical portion symmetrical to the axis of the cylindrical first portion and terminating adjacent the entry of the discharge line.

3. The measuring cell of claim 1, wherein said second means is disposed in the peripheral surface of the first portion.

4. The measuring cell of claim 1, wherein said first means is displaceably disposed in the inner chamber parallel to the longitudinal axis.

5. The measuring cell of claim 1, further comprising means for variably adjusting the volume of the inner chamber.

6. The measuring cell of claim 1, wherein the constricting means comprises a nozzle inserted in the input conduit.

7. The measuring cell of claim 1, wherein the constricting means comprises a nozzle inserted in the input conduit.

8. The measuring cell of claim 1, further comprising a thermal insulating jacket surrounding the inner chamber.

* * * * *